United States Patent [19]

Hoberman

[11] Patent Number: 4,889,992
[45] Date of Patent: Dec. 26, 1989

[54] AUTOMATIC INFRARED MICROORGANISM DETECTION INSTRUMENT

[76] Inventor: Max Hoberman, P.O. Box 7628, Jerusalem, Israel, 91076

[21] Appl. No.: 119,544

[22] Filed: Nov. 12, 1987

[51] Int. Cl.$^4$ .............................................. G01N 21/03
[52] U.S. Cl. ................................... 250/343; 250/576; 435/39; 436/165
[58] Field of Search ........................ 250/343, 576, 573; 356/246; 435/808, 807, 39; 436/165; 422/83

[56] References Cited

U.S. PATENT DOCUMENTS

| | | | |
|---|---|---|---|
| 3,860,347 | 1/1975 | Jones | 356/246 |
| 3,941,660 | 3/1976 | Mirsky | 435/35 |
| 3,963,927 | 6/1976 | Bruce et al. | 250/338.1 |
| 3,997,404 | 12/1976 | Waters | 435/35 |
| 4,030,979 | 6/1977 | Zuber | 435/39 |
| 4,197,369 | 4/1980 | Weaver | 435/12 |
| 4,250,266 | 2/1981 | Wade | 435/289 |
| 4,370,553 | 1/1983 | Waycaster et al. | 250/343 |
| 4,648,396 | 3/1987 | Raemer | 128/204.22 |
| 4,729,661 | 3/1988 | Bell | 356/436 |

Primary Examiner—Janice A. Howell
Assistant Examiner—Constantine Hannaher
Attorney, Agent, or Firm—Ralph R. Roberts; Patrick J. Pinto

[57] ABSTRACT

This invention relates to an instrument for the detection of microorganisms in a culture media by means of the measurement of the gaseous products generated during bacterial metabolism, without the need for extracting the products of metabolism from the culture vessel in order to perform the measurement. A special vial containing a gas-liquid separation system permits the measurement through the walls of the vial by determination of the infrared absorption by the gaseous contents within the vessel. While intended primarily for blood-culture testing, the method is applicable to other microbiological and physical chemistry investigations where changes in gas concentrations must be determined in a simple, convenient manner. An alternate embodiment is shown and described whereat a high concentration of gas is present and the infrared energy path is too long for accurate measurement.

38 Claims, 6 Drawing Sheets

AUTOMATIC INFRARED MICROORGANISM DETECTION INSTRUMENT

BACKGROUND OF THE INVENTION

1. Field of the Invention

This invention relates to an automatic instrument adapted to detect microorganisms in a culture media and by means of measurement of the level of gaseous products, evaluate these media. This measurement is achieved without the need for extraction of the product.

2. Description of the Prior Art

The measurement of bacterial microorganisms has been addressed in many issued patents, among which are: Pat. No. 3,941,660 to MIRSKY as issued March 2, 1976. This patent refers to the use of radioactive material which generates radioactive $CO_2$ in metabolism, which Applicant's invention is specifically intended to eliminate because of the legal restrictions involved in handling radioactive materials. In particular, this detection system uses sharp instruments or needles which must be inserted through the vial septums, with the likelihood of clogging, and the need to alter vial orientation to maintain septum integrity. Applicant's invention, hereinafter detailed and claimed, is a non-invasive method for measuring gas concentration in sealed containers subject to agitation of the liquid contained in the containers.

Also of note is BRUCE et al, (U.S. Pat. No. 3,963,927) as issued June 15, 1976. This patent shows apparatus for measuring the increase in concentration of $CO_2$ generated by insect respiration which is allowed to build up in a sample cell to a degree sufficient to be measured by a Luft-type infrared $CO_2$ gas analyzer.

Also of note is WATERS (U.S. Pat. No. 3,997,404) as issued December 14, 1976. This patent shows an apparatus and method which describes measurement of radioactive $CO_2$ generated by bacterial metabolism through gas-tight cells having a light-permeable wall section, although infrared is not employed, rather scintillation counting. Also noted was WEAVER (U.S. Pat. No. 4,197,369) as issued April 8, 1980. This patent describes the use of a permeable membrane and means for measuring directly the amount of vaporous product passing through the membrane through the use of a mass spectrometer. While a membrane does provide a gas-liquid separation means, using the teaching of WEAVER the membrane would be subject to clogging by turbid liquids which would impede gas transport and so is not useful as a low-cost, commercial instrument where sample vials pass through a number of hands, with attendant turbulence before measurements are made.

Also noted is WADE (U.S. Pat. No. 4,250,266) as issued February 10, 1981, which provides apparatus such as the use of a carousel mentioning a "fully automated incubation and detection system," including a closed incubated chamber including agitation of culture bottles and indexing of trays, with the periodic measurement of the electrical parameters of the contents of each bottle with the display and results, all controlled by a microprocessor. The method of measurement of bacterial growth in WADE includes measurement of electrical conductivity, i.e., the magnitude of the voltage measured when a current is passed through the fluid. This measurement is of the growth of the microorganisms in the culture. Physical changes in the culture can affect electrical conductivity, whereas the generation of $CO_2$ is prima facie evidence of actual bacterial metabolism.

SUMMARY OF THE INVENTION

This invention may be summarized, at least in part, with reference to its object, which is to provide, and it does provide, an instrument for the measurement of change in the charge sample in a closed vessel, utilizing a source of infrared specific to its use. This instrument has the infrared energy directed through a removable container member containing the liquid to be measured. The emerging infrared energy is measured and evaluated to interpret this magnitude.

Before the availability of automated microorganism detection instruments, testing was done manually. Samples were applied to agar-nutrient cultures in Petri dishes or introduced into culture vials where they were examined visually from time to time by a medical technologist to detect the formation of growth colonies or changes in turbidity indicating the presence of microorganisms. Measurement of bacteria in blood cultures not only greatly facilitates diagnosis of diseases, but enables drug susceptibility testing by permitting the determination of the efficacy of different medications by the in-vitro testing of blood samples.

Early automated blood culturing systems detected the presence of bacteria based on the measurement of products of metabolism, rather than depending upon subjective observations of visible growth. Radioactive carbon in the nutrient in a closed vessel, when metabolized by bacteria, produced radioactive carbon dioxide which could be detected and measured. However, objections of laboratory personnel, as well as legislation prescribing stringent handling and disposal procedures, mitigated against widespread use.

Most advanced instrumentation today utilizes a non-radio-active carbon in the nutrient substrate which generates ordinary carbon dioxide when metabolized by bacteria. The gas in the sample vial is then tested and the concentration of $CO_2$ determined as a measure of the presence and growth of bacteria. One instrument requires the insertion of two needles through the septum of the sample vial, one to withdraw the gas sample and the other vented to a control gas and for pressure equalization. The withdrawn gas is analyzed by infrared spectrophotometry techniques to measure carbon dioxide. For speed and economy, many vials must be processed on one instrument, so sterilization, generally by ultraviolet radiation, must be done between each vial test to prevent cross-contamination from one vial to another. Too, the frequent insertion, withdrawal and sterilization of needles and the need to maintain septum integrity make frequent change of needle orientation mandatory and also necessitate changing them often. The foregoing makes for a cumbersome and expensive instrument which the present invention greatly simplifies and improves. While it is apparent that the invention is applicable to a wide variety of gas concentration measurements, the description herein will be in terms of $CO_2$ measurement due to bacterial metabolism in blood cultures.

The invention described here is an instrument which avoids the need for withdrawing gas samples from test vials by providing means for the measurement of $CO_2$ concentration in situ, that is, through the walls of each vial by means of a unique infrared spectrophotometry technique.

In infrared spectrophotometry, particularly non-dispersive spectrophotometry of carbon dioxide, infrared energy is generated in the band of approximately 4.35 microns, the absorption band of $CO_2$, either by means of a suitable black body radiator with appropriate filter to reject other wavelengths, or by means of a specific frequency infrared generator achieved by exciting gas mixtures containing carbon dioxide and other gases such as helium, nitrogen and xenon, to lower striking potentials with high-frequency, high-voltage energy. The infrared energy produced is directed through the unknown gas to be analyzed. The presence of $CO_2$ is manifested by the absorption of some of this energy. The degree of absorption, measured by a suitably calibrated detection system, is then the measure of $CO_2$ concentration.

Infrared (IR) detectors commonly used today include thermal detectors, such as thermopiles or thermocouples, microphone detectors which detect the expansion of a gas upon absorption of IR energy by altering the spacing between the plates of a sensitive capacitor, and molecular detectors such as pyro-electric detectors and the lead salt detectors: lead sulphide and lead selenide. Since some of these respond only to changes of incident IR, means must be provided, either by chopping the IR beam or by pulsing the IR generator, to generate a varying rather than a steady state IR source. Too, synchronous electronic detection may be employed, where the detection system is activated in synchronism with the pulses of infrared energy, greatly narrowing the information bandwidth and improving signal-to-noise ratio. The present invention is applicable to either the steady state or pulsed IR beams.

In this invention, unlike previous bacterial measurement instruments, incubation and agitation to stimulate bacterial metabolism is accomplished within the instrument itself, eliminating the need for separate incubation and agitation devices, and greatly simplifying and shortening the often extended time required for testing, particularly of slow-growing myco-bacterial cultures.

The information processing and functional control of the various subsystems is done in a microprocessor controller which includes an algorithm for detecting the essentially geometric growth of slow metabolizing myco-bacteria so that positive tests are identified at the earliest possible time. This controller is programmed to record the zero base $CO_2$ concentration at the beginning of the test procedure to permit compensation for slight manufacturing differences between vials. Calibration is also performed between vial tests so that repeatability and reliability of measurements is maintained. Further advantages, including bar code identification, automatic printout of results and flagging of positive vials, will be explained by the description of the invention which follows.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of an automated infrared microorganism detection instrument as adopted for use in ascertaining the measurement of bacterial products and showing a preferred means for measurement without a need for extracting said products of metabolism from th culture vessel. This specific embodiment has been chosen for the purposes of illustration and description as shown in the accompanying drawings wherein:

BRIEF DESCRIPTION OF THE DRAWINGS

FIGS. 7 A and 7 B represent a graph of the infrared radiation transmitted through a vial in motion;

FIGS. 8 A and 8 B represent graphs of bacteria population as a function of time;

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

DESCRIPTION OF THE PREFERRED EMBODIMENT

Figures 1, 2, 3, 4:
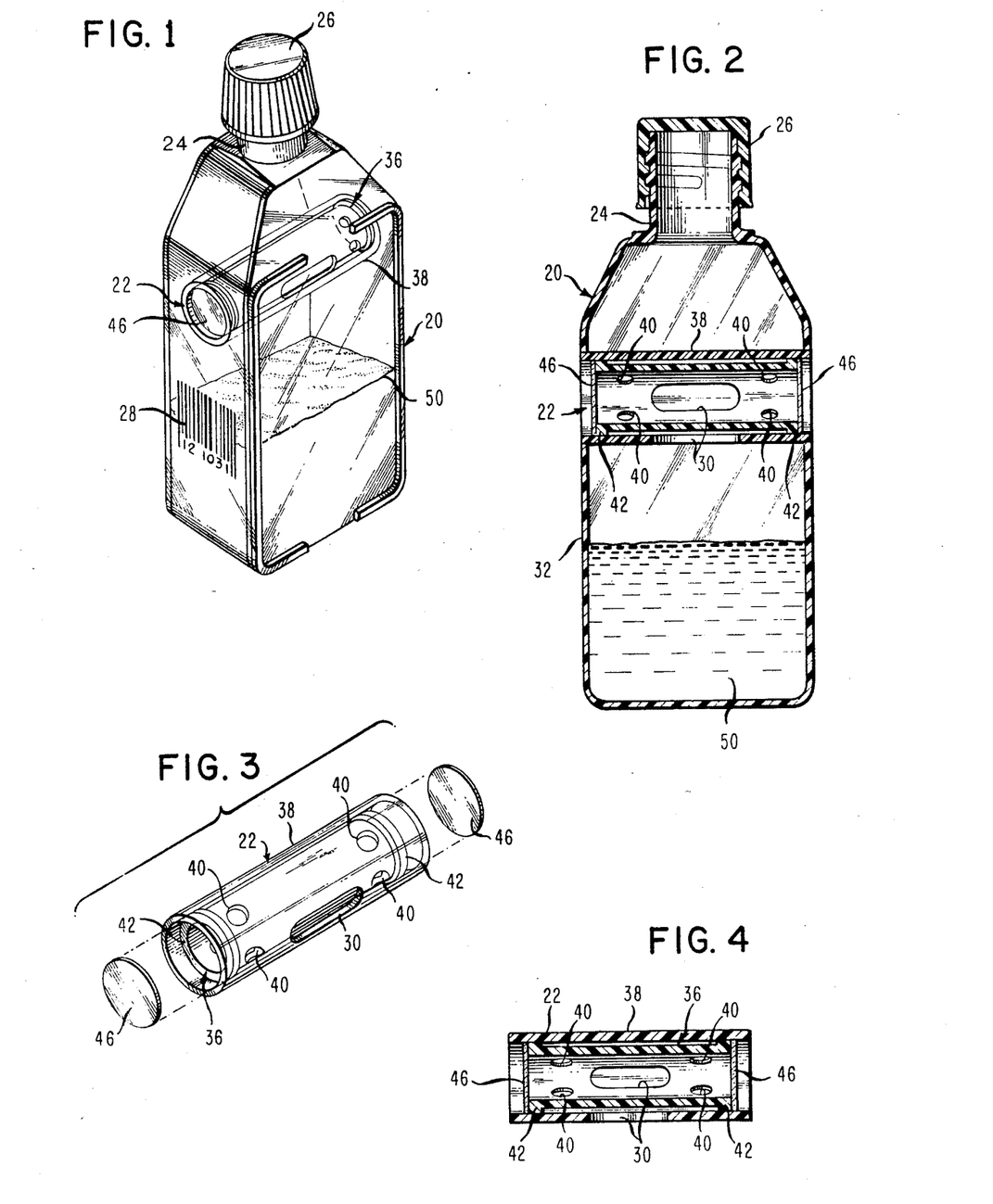
FIG. 1 represents an isometric view of the vial specially constructed for Infrared measurement of gases produced in a vial.
FIG. 2 represents a side sectional view of the vial of FIG. 1 and depicting the interior construction thereof.
FIG. 3 represents an isometric, and partly diagrammatic, view of the core module used in the vial.
FIG. 4 represents a sectional side view of the core module of FIG. 3 in an assembled condition and adapted for securement in the vial.

In FIG. 1 is depicted a plastic vial or container used in practicing this invention. This vial is shown as rectangular as this configuration requires a minimum of space and insures orientation and alignment with a detection means to be described hereinafter. This vial or container is generally identified as 20 and has a longitudinally arrayed core module 22 secured therein and therethrough. This core module is mounted and secured so as to be leak-proof. Also shown is a neck portion 24 which is conventional and whose distal end is closed with a stopper or cap 26 of resilient material which provides means sufficient to permit insertion of and subsequent withdrawal of a needle of a syringe, leaving this resilient closure means, more or less, self-sealing as to passage of fluid (particularly blood) and gases. A screw-on cap is depicted in the sectional view of FIG. 2, but other closing means is contemplated. Also seen in this view is bar indicia 28, which is like that now used as identification on many articles. This bar identification enables an associated microprocessor to identify this particular (or any similar) container by known electronic detection means.

FIG. 2 shows the core module 22 with a plurality of slots 30 and, as secured in the container 20, this core module has the slots to the sides and/or bottom. In the preferred arrangement, the container 20 is cemented to outer wall 32 so that three slots 30 are disposed to be at the side and the bottom. The top portion of the core is absent of slots as fluid may be brought to the containers through the cap 26. Fluid is also supplied to the interior of the container 20 through this top with or without the cap 26 removed.

FIG. 3 shows a baffle insert, generally identified as 36. This insert is a tubular member 38 having vent holes 40 at each end of said tubular member. At each end of member 38 is an enlarged collar portion 42. The outer diameter of these collar portions is sized to be slideable in the interior diameter of core module 22 and, after positioning, this insert is secured in and made fluid-tight in the core module 22 as by adhesive. In mounted and secured condition, the baffle insert 36 is fixed so that these vent holes 40 are positioned so as to be exterior of the slots 30. At each end of this insert 36 is an IR (infrared) translucent window 46, which window may be molded or cemented to the ends of the baffle insert 36. The length of the baffle sleeve slots 30 and of the baffle insert 36 determines the distance between translucent windows 46, which is selected to be optimum for the $CO_2$ concentration variations expected. For high concentration, and therefore great absorption, the distance should be small, and for low concentrations a long absorption path is desirable. The entire baffle assembly, which includes core module 22 and baffle insert 36, is then secured, usually by cementing into the plastic vial 20. The vial itself is sealed by cap 26 to permit the aseptic introduction of a blood sample by means of a hypodermic syringe.

Figure 5:
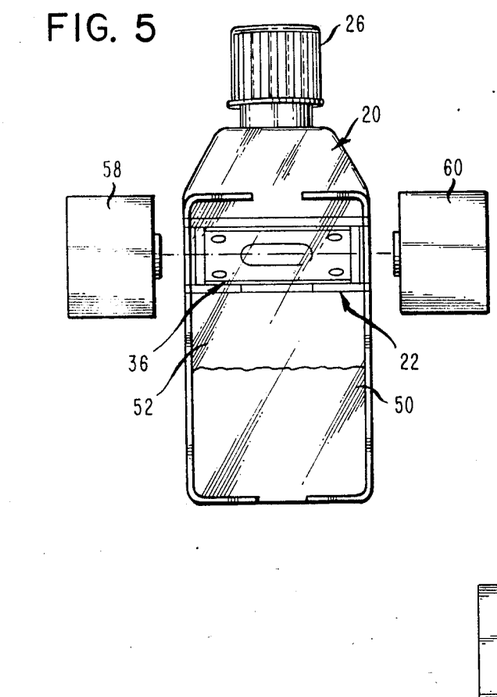
FIG. 5 represents a diagrammatic side view of the vial of FIGS. 1 and 2, and diagrammatically showing this vial being brought to and between an IR source and a detector.

In FIG. 5 is a schematic showing of the container 20 with the core module 22 and the baffle insert 36 in mounted condition. The cap or stopper 26 may be removed for the insertion of a culture-broth identified as 50. The amount of broth is less than the volume needed to reach the core module. This space above the culture-broth 50, identified as 52, allows gas to be generated. The cap or stopper 26 is secured in place before blood or the like is added by a hypodermic needle (not shown). Within the vial 20 is culture-broth 50 which is specific to the bacteria to be detected. A bar code indicia 28 (FIG. 1) is printed or otherwise marked on one end of the surfaces of the vial. It has been found that several materials, including Polyester; methyl methacrylate polymer (Acrylic) and thin glass discs, impermeable to $CO_2$ have sufficient transparency to infrared to make suitable windows for the IR core. When assembled as shown in the diagrammatic view of FIG. 4, the peripheral vent holes 30, offset from the baffle sleeve slots 30, form a gas-liquid separation system which substantially prevents liquids or froth generated by the bacterial metabolism process from entering the baffle insert 36 while nevertheless permitting ready diffusion therein of carbon dioxide generated within the vial. Without a gas-liquid separation means, measurement directly through the transparent walls 32 of the vial 20 could be greatly affected by opaque liquid or froth in the path of the infrared beam. Other forms of gas-liquid separation systems such as semi-permeable membranes, and plastics permeable to $CO_2$ such as polyethylene, can also be used for this purpose. As an optional feature, within each vial may be added a small permanent magnet, suitably encased in an inert plastic as used in magnetic stirring devices to agitate the blood-culture-broth mixture when energized by an external varying magnetic field to stimulate bacterial metabolism as will be further described herein.

Figure 6:
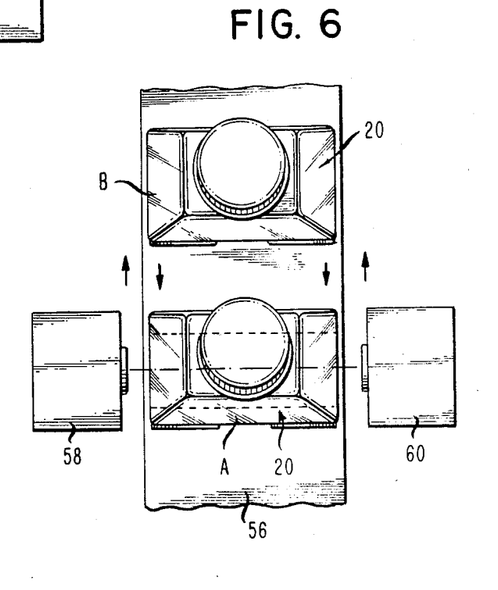
FIG. 6 represents a diagrammatic top view of a plurality of vials as said vials are brought in way of an IR source and detector.

In FIGS. 5 and 6 are shown side and top views of a source of infrared, either pulsed or continuous, separated in longitudinal position from an IR detection system. A transport means, such as a conveyor belt, a carriage 56 or movable means, into which test vials 20 have been placed, is arranged to move transversally, positioning the test vials between a source of IR 60 and a detector 58. Whereas FIGS. 5 and 6 describe a belt or carriage 56 for moving the vials 20, the invention is equally applicable where the vials are stationary and a carriage transports the IR source-detector arrangement. The motion may be either continuous or intermittent, with the motion stopping when IR core module 22 and the line of IR source 60 and detector 58 are in alignment, thus permitting the measurement of IR over a longer period of time, that is, integrating the IR energy to provide greater signal-to-noise ratio or for averaging the energy received to enhance accuracy. Vial 20 is shown positioned directly between the IR source 60 and the detector 58 with another like vial 20 separated transversally.

Figure 7A:
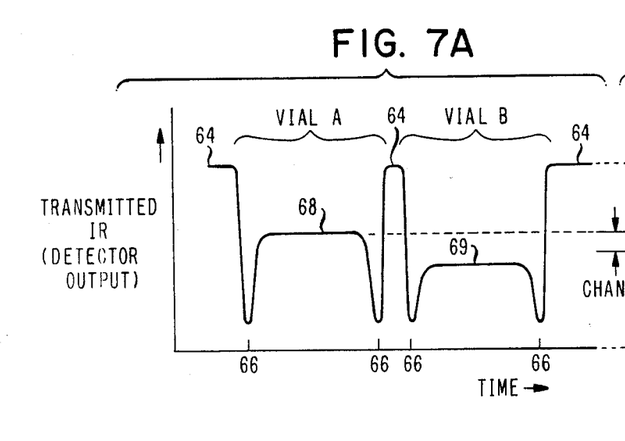
Figure 7B:
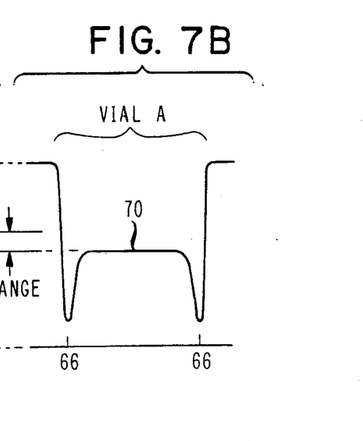

FIGS. 7 A and 7 B represent graphs of the infrared radiation transmitted through the vial 20 when there is continuous, relative transverse motion between the vial and the infrared beam. At 64 is shown the large IR signal received at the detector 58 when there is a clear field unobstructed by a vial. When the edge of a vial intercepts the direct line of the IR beam, say at time $t_o$, the received signal is attenuated to the value, shown as 66 in the graph. Some short time later, the IR signal is transmitted to the detector through the IR core of the vial and there is attenuated only by the windows 46 and any IR absorption which occurs due to the $CO_2$ present within the vial. The received signal intensity may then be at a level shown as 68 in FIG. 7 A. With further relative motion between the vials 20 and the IR axis, the signal is again attenuated to the value 66 at the second edge of the vial and is again at its maximum 64 between vials when there is only the obstruction of the atmosphere between vials. The process is repeated for a second following vial, shown in FIG. 6, where the received IR 69 in FIG. 7 A may be different because of a different concentration of $CO_2$ within this second vial. At some time later, if metabolism of bacteria with its generation of $CO_2$ has meanwhile occurred in the first of the vials, more infrared energy would be absorbed in its passage through the vial core, and the IR received at detector 58, when that vial is measured again, may then be represented as 70 in FIG. 7 B. The change in detector outputs 68 to 70 is then a measure of the $CO_2$ concentration within that first vial.

The signal amplitude of the IR transmitted between vials, unobstructed by a vial, is shown as 64 in FIG. 7 A. However, if the measurement is made in air, there will be some absorption of IR because of the small $CO_2$ concentration in the atmosphere. to further increase the accuracy of measurement by eliminating this effect, the measurements may be made in a sealed portion of the instrument in an inert atmosphere such as nitrogen, or alternatively in one which includes a $CO_2$ scavenger such as lithium hydroxide. The IR transmitted between vials will then be essentially free of absorption effects and so provides a convenient, stable, physical calibration reference for comparison with the IR transmitted through the vial. Alternatively, the signal transmitted through this unobstructed path can be used as a reference to adjust the intensity of the IR source or the gain of the system or its law can be programmed into the microprocessor algorithm to compensate for change or degradation of system parameters due to all causes. Alternatively, and not shown, is a sealed tube with IR transparent windows which can be filled with inert gas or IR transmitting substance and be positioned in this space between vials to provide a stable reference signal during interval 64 of FIG. 7 A for the purposes described.

Figure 8A:
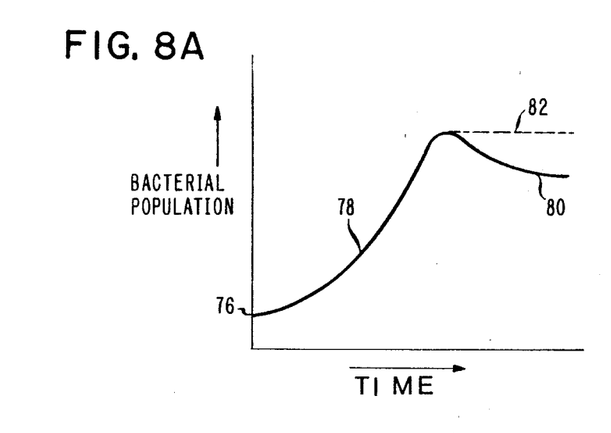

FIG. 8 A is a graph of the growth of bacterial population as a function of time when the bacteria have been cultured at an appropriate temperature, say thirty-five degrees to thirty-seven degrees Celsius, in a suitable medium. Beginning with an initial concentration shown as 76, bacterial population increases at an approximately geometric (slope) rate 78 until all of the nutrient is exhausted at 80. Subsequent to this, population may decrease as bacteria die off, or the bacteria may change to a dormant form and remain at a stationary level 82.

Figure 8B:
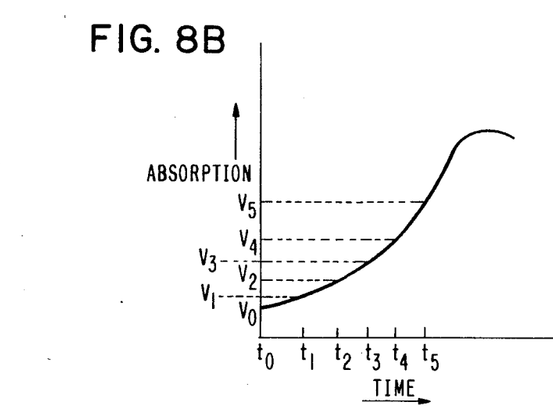

In FIG. 8 B is shown the IR absorption in the carbon dioxide, generated by the process depicted in FIG. 8 A, as a function of time. For a constant t, the geometric increase in $CO_2$ concentration as measured by IR absorption may be expressed as:

$$V_2 - V_1 = k(V_1 - V_o)$$

$$V_3 - V_2 = k^2(v_i - v_o)$$

in general:

$$V_{n+1} - V_n = k^n(V_1 - V_o)$$

Evidence of this geometric growth law is then definite proof of bacterial metabolism and is an accurate and convenient method for virtually eliminating "false positives," that is, apparent increases in $CO_2$ concentration because of momentary errors in instrumentation, noise, obstruction of the IR beam by dirt or dust, or any spurious phenomena.

Figure 9:
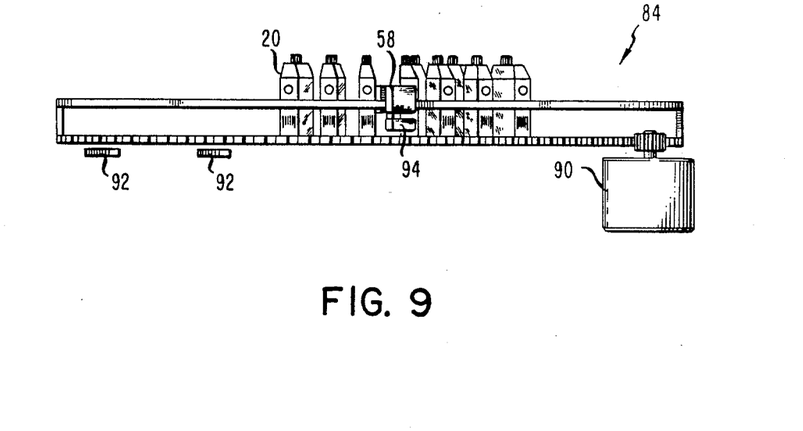
FIG. 9 represents a side view, partly diagrammatic, of a plurality of the vials of FIG. 1 as transported by a carousel so as to be in way of an IR source and bar indicia detector.
Figure 10:
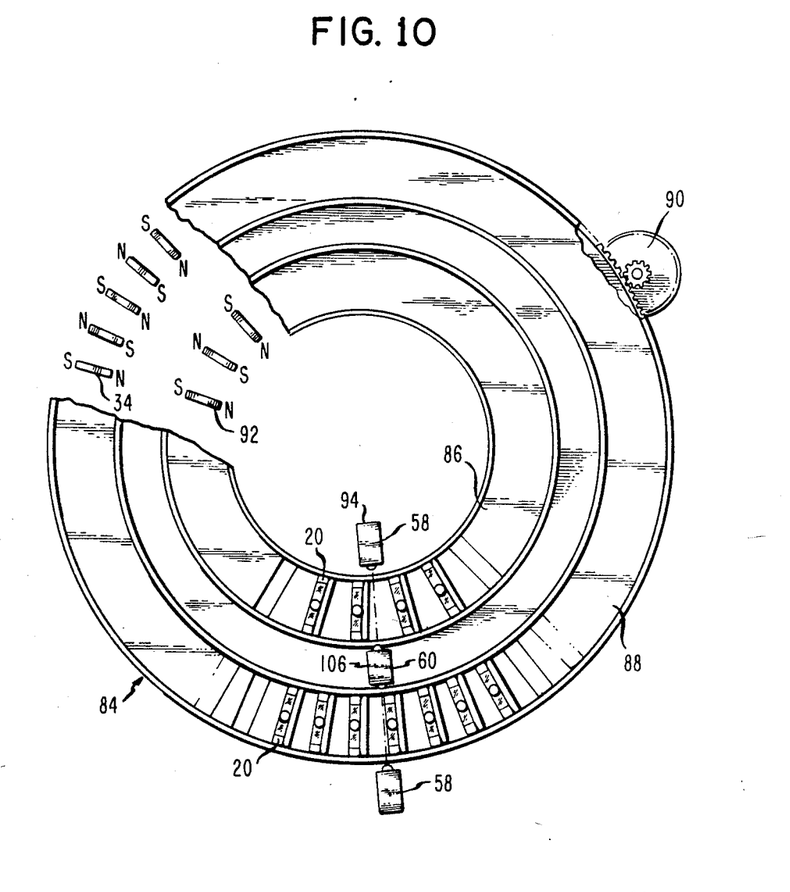
FIG. 10 represents a plan view of a carousel, diagrammatically showing two rows of vials movable to bring said vials in the path of infrared energy, with a portion broken away to illustrate the use of magnets to agitate the culture broth.

An operational sequence of this invention may be described by reference to FIGS. 9 and 10 and the microcontroller block diagram of FIG. 11. In FIGS. 9 and 10, a rotating carousel, generally identified as 84, includes a movable carriage inner ring 86 and a movable carriage outer ring 88 which are driven at a slow rate of about one revolution per 30–60 minutes by motor 90. In each of the rings 86 and 88 are suitable slots into which the sample vials 20 of FIG. 1 may be inserted so that a bi-directional specific source of IR 60 may direct IR energy through the IR core 22 of a vial 20 as in FIG. 1. IR detectors 58 are positioned to detect this IR energy exiting from the IR core of each vial in turn as the carousel carriages rotate. Mounted radially in stationary position in close proximity to the underside of the carousel 84 at several angular locations are permanent magnets 92, arranged with opposing polarity, which agitate a magnet (not shown) within each test vial 20 as it rotates so as to stir the culture-broth and stimulate metabolism. The several magnets 92 are depicted arrayed so that agitation will occur as the carousel is rotated. The magnet carried in the container 20 is not shown as the size and protective covering is a matter of selection to accommodate the culture in the container. No patentable distinction is ascribed to the construction of the magnets. Bar code readers 94 are mounted adjacent to the rotating carousel at its internal and external peripheries and are positioned to read the vial bar indicia codes and a bar code representing the particular bin into which a vial has been inserted as the vials pass.

Figure 11:
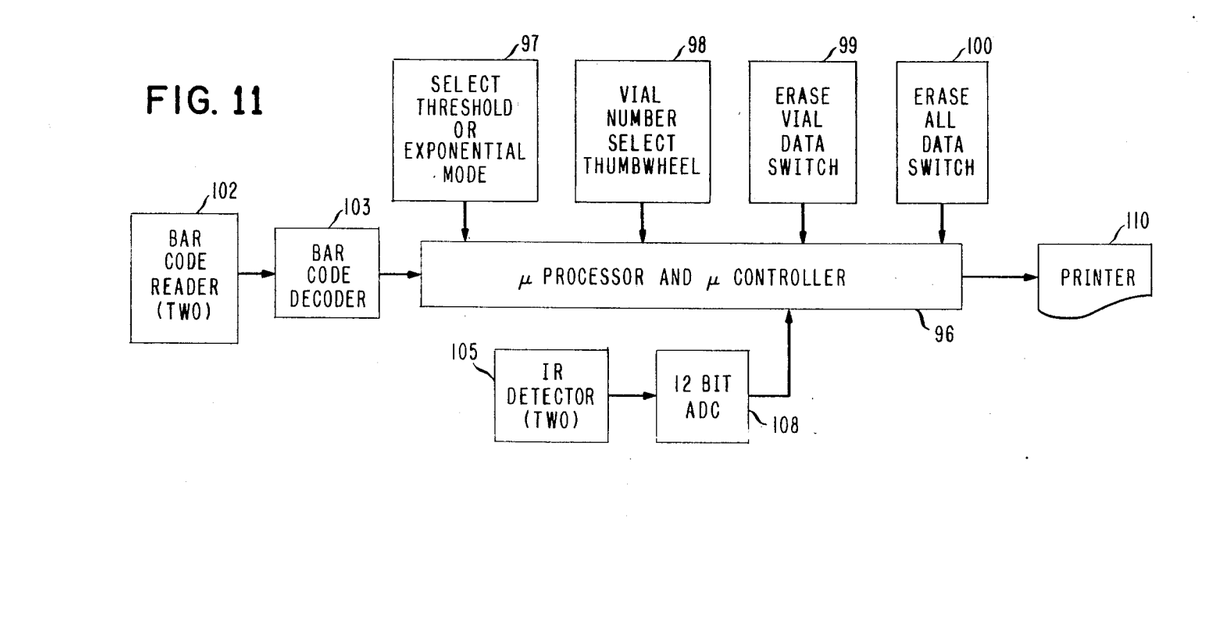
FIG. 11 represents a block diagram illustrating the electronic controls and evaluation of the detection process

BLOCK DIAGRAM OF FIG. 11

The above-described detection apparatus has electronic control and operations utilizing a microprocessor and controller, identified as 96. Controls are indicated as "Select threshold or experimental mode," identified as 97. "Vial number-select thumb wheel" is identified as 98. "Erase vial data switch" is identified as 99, and "Erase all data switch" is identified as 100. These are all connected to the microprocessor 96 to control the operation thereof. A "bar code reader," identified as 102, reads bar identification indicia 28 from each vial as it passes and feeds this information to a "bar code decoder," identified as 103, and from this decoder information is fed to the microprocessor 96.

Also feeding information to the microprocessor 96 is the IR detector, identified as box 105. When and as apparatus such as the carousel 84 of FIGS. 9 and 10 is utilized, the source 60 may be two in number and secured in a housing identified as 106 (FIG. 10). This information is fed to a "12 Bit ADC" storage media 108, with these information signals sent to the microprocessor 96. This result is displayed or printed on tape 109 (FIG. 12) by a printer, identified as 110. As a vial intercepts the line of IR source-detector axis 58–60, the IR source is energized and the vial 20 and location-identifying bar codes are read, decoded and stored in the microprocessor memory 96 of FIG. 11. Simultaneously, the IR detected by detectors 58, as appropriate, is digitized in a 12 bit analog to digital converter 108 and stored in the microprocessor memory. These three numbers: bin number, vial number and the initial value of detected IR are printed out sequentially in the following form as an example:

| (Bin Number) | (Vial Number) | (Detected IR) |
|---|---|---|
| 32 | 195112 | 3.45 |

| (Bin Number) | (Vial Number) | (Detected IR) |
|---|---|---|
| 33 | 171130 | 3.41 |

At each subsequent pass of the vials 20 on the carousel 86 turntable, the process is repeated and the detected IR compared with the initial reference value. If the change in the detected IR exceeds the reference value by a pre-settable threshold amount, indicating bacterial metabolism, the location bin number, vial identifying number and the new IR detected output are printed out. Alternatively, in the geometric detection mode of operation, at least four consecutive readings of detected IR are compared and only that vial which indicates the generation of $CO_2$ at a geometric rate would have its parameters printed out as a "positive." In either case, no printout is done if the presettable IR threshold is not exceeded or if, in the geometric detection mode, the geometric growth rate is not evidenced. However, the initial reference value is stored for comparison with the data generated at each subsequent pass of the vials, and in the geometric mode consecutive readings are stored and the oldest reading erased as each pass of the carousel carriage generates new information. Means are provided in the microcontroller for erasing any or all data as desired by the operator.

While this description is for the case where the IR source-detector axis is stationary and the carousel transports the vials, it is equally appliable where the vials are stationary and the IR source-detector axis is rotated by the carousel, in which case the magnetic stirrer would have to be rotated with it. Alternatively, a conventional magnetic stirrer consisting of a rotating AC field may be located at one point under the carriages, although for some applications the speed of stirring may be excessive.

Figure 12:
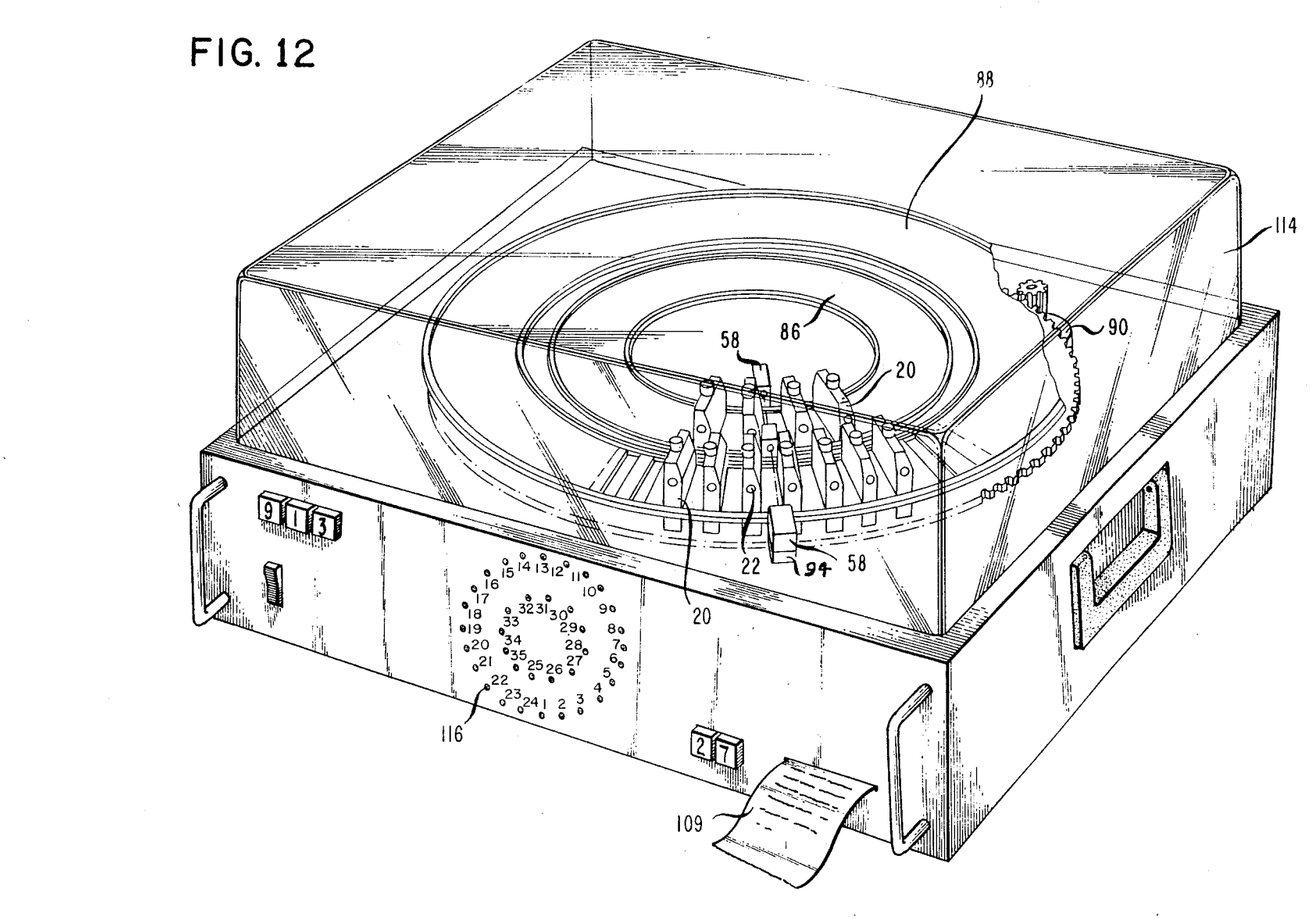
FIG. 12 represents an isometric view of a carousel apparatus and depicting a cover providing means so that the interior is maintained at a desired concentration.

EMBODIMENT OF FIG. 12

FIG. 12 illustrates the complete assembly of the described invention wherein 114 is an identification of a transparent, thermally insulating cover enclosing the vial chamber. By means of thermostatically controlled heaters, the vials and contents are incubated as desired. Enclosure also permits operation with a purged, $CO_2$-free atmosphere. Indication of which vial is being measured at a particular time and illumination of vial numbers of those showing positive tests are displayed on a circular LED display 116 corresponding to the arrangement of vials within the enclosure.

It is to be noted that the cap is attached to an upwardly-extending neck, but it is also contemplated that other configurations may be used and it is only needed that the resilient cap be above the culture medium. It is also to be noted that slots are depicted as formed in the core module 22. It is also contemplated that passageways into this core may be by other means such as holes. Desirably, the gases generated pass through these passageways to and through the apertures in the internal member so as to be in way of the infrared energy beam.

EMBODIMENT OF FIGS. 13, 14, 15 AND 16

The metabolism of some microorganisms is accelerated in an atmosphere initially rich in carbon dioxide. Concentrations of $CO_2$ as high as five percent have been found to be advantageous for this purpose. However, the absorption of $CO_2$ specific infrared radiation in such atmospheres is so great, being as high as thirty percent to forty percent per millimeter for concentrations in the range of four percent to five percent $CO_2$, that the long absorption path of the construction shown in FIG. 4 would absorb virtually all the entering IR so that a negligible amount would exit to be measured. Reduction of the length of the baffle insert of FIG. 3 would mean that the IR traverses the remaining length of the baffle sleeve of core module 22 in the ambient atmosphere which, if air containing a significant amount of $CO_2$, adds an uncertainty to the amount of IR absorption measured. This would dictate that the ambient atmosphere be purged of $CO_2$ by one of the methods described. A construction which allows the use of a short-length absorption path without these disadvantages is shown in FIGS. 13, 14, 15 and 16.

Figure 13:
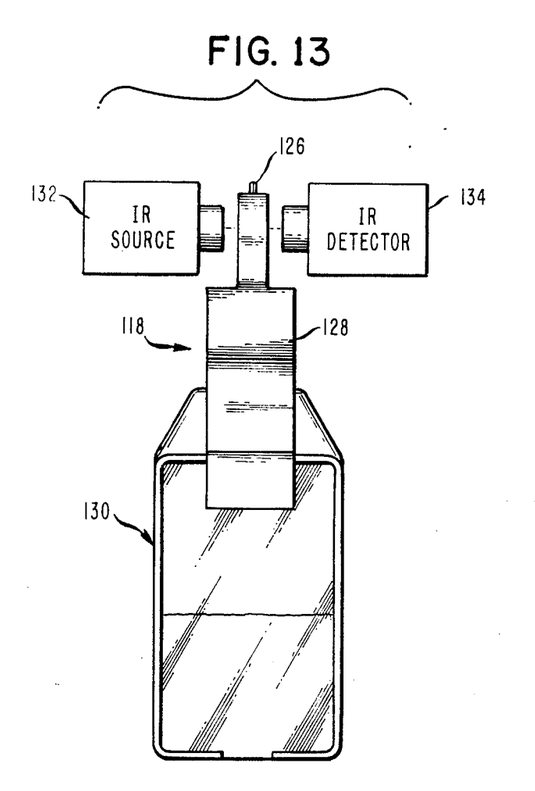
FIG. 13 represents a vial and detector means with the gases, as produced, evaluated or measured in an exterior collector, this collector shown mounted on a vial and with the IR source and detector positioned above the vial.
Figure 14:
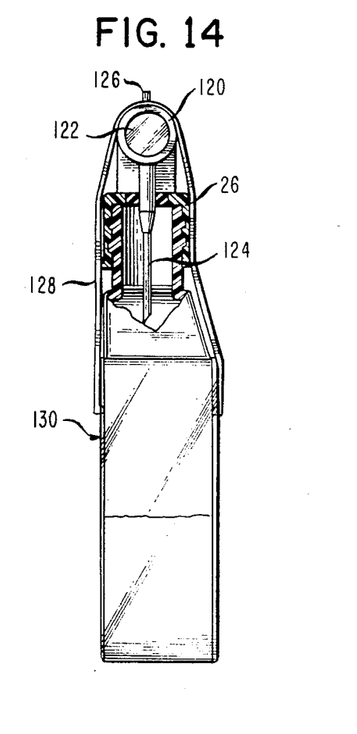
FIG. 14 is a partly sectional view of the vial and collector, this view partly diagrammatic and transverse of FIG. 13.
Figure 15:
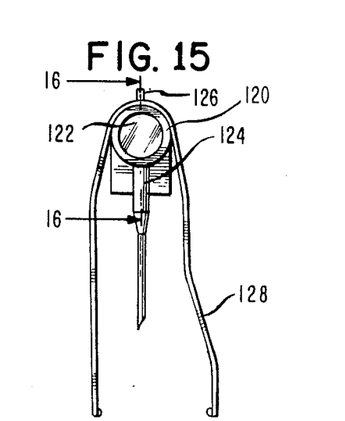
FIG. 15 is a view of the collector assembly of FIG. 14, but absent the vial.
Figure 16:
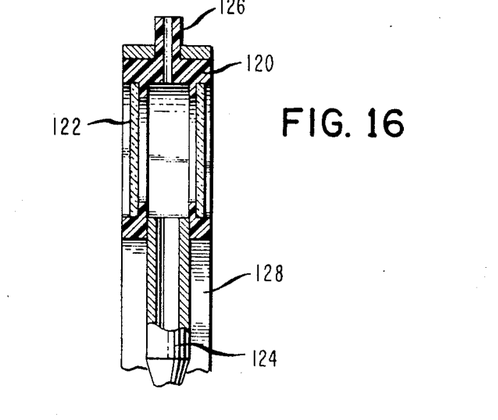
FIG. 16 represents a sectional, partly fragmentary view of the collector, this view taken on the line 16—16 of FIG. 15 and looking in the direction of the arrows.

An alternate absorption cell device or assembly 118, as shown in FIGS. 13 and 14, includes a retaining ring, identified as 120, and has IR transparent windows 122 and provides a very close space therebetween. A hypodermic needle 124 is in flow communication with the space between the windows 122. At the top of ring 120 there is provided a unidirectional valve or vent 126 which is mounted so that gases entering through the needle fill the absorption cell and can be vented through the valve or vent. (Bacterial metabolism, generating an increase in gas pressure, and the inclusion of a unidirectional venting means from the absorption cell, provide a self-cleaning feature to prevent clogging of the hypodermic needle 124.) A bracket or bent strap 128 is attached to and supports the ring 120, and facilitates the removable mounting of the assembly 118 upon the sample vial 130 as depicted in FIG. 14. It is to be noted that sample vial 130 is very similar to vial 20, seen in FIG. 1, but this vial has no core or baffle insert. The cap 26 is like that discussed above and is of resilient material so that the needle 124 may be inserted and, when desired, withdrawn. After a blood sample is introduced into the sample vial 130 as described above, the absorption cell assembly 118 of FIG. 13 and is mounted upon the vial, with the hypodermic needle 124 piercing the vial septum cap 26 so that the gases generated within the vial 130 are introduced into the absorption cell assembly 118 and the space therein. With this construction, an IR source, identified as 132, and an IR detector 134 are arrayed so as to be mounted in close proximity to the short absorption cell 118, thereby enhancing the instrument accuracy and eliminating the need for operation in a $CO_2$ purged atmosphere.

The above-identified apparatus also provides novelty for a method of measuring the changes in concentration of gas or gases in a vial, utilizing infrared energy for such measurement, this method including the steps of:
providing a vial adapted to receive and retain a culture fluid without leakage of fluid;
disposing a resilient cap means at the upper end of the vial, said cap means adapted for penetration by a hollow needle and the like, enabling the adding of at least one component to the closed vial;
providing means in a core module for passing therethrough of infrared energy from a source to a detector, and further providing this core module with a sealing exclusion of the interior of the vial to atmosphere, and forming in said core module:
a plurality of passageway means from the interior of said vial to and through said passageways;
a sized receiving bore in said core module and therethrough;

positioning in said core module in the vial so as to be in a determined relationship to the support means of the vial;

mounting a baffle insert in the bore of said core module, with said baffle insert in a mounted condition having means for excluding exterior air and the like from entering that bore portion occupied by said baffle insert, and forming said baffle insert with:

a tubular insert having enlarged end portions adapted to fit within said bore of the core module, and with the intermediate portion formed with a reduced tubular portion providing a space between the outer portion of the insert and the bore of the core module;

a plurality of hole-like passageways through the walls of said tubular insert, these passageways adapted to provide flow means for gases from the interior of the vial through the passageways in the core module, thence through the hole-like passageways in the baffle insert into the inner portion of the baffle insert, these hole-like passageways in the reduced tubular portion, and attaching a window means to each end of the tubular insert, with each window adapted to pass infrared energy specific to gases produced in the vial;

inserting in said vial a liquid of specific volume and composition, which volume, when placed in the vial, is below the core module when the vial is arrayed for and in use;

adding at least one other material to the liquid in the vial and, with this addition, generating a gas which flows to the interior of the baffle insert;

providing a source of infrared energy and a detector arrayed so as to receive said energy and evaluate said received energy and send said evaluations as electrical signals for measuring the magnitude of said infrared energy and interrupting the magnitude of emerging infrared energy as a concentration of gas as produced within the vial.

While I have disclosed a preferred embodiment, description and application of the invention, other modifications not specifically disclosed or referred to will be apparent to those skilled in the art in light of the foregoing description, which is intended to provide concrete examples of a preferred embodiment and application clearly disclosing the invention and its operating principles. Accordingly, the invention is not limited to any particular embodiment or configuration of component parts thereof. All alternatives, modifications and variations of the present invention which fall within the spirit and broad scope of the appended claims are intended.

What is claimed is:

1. An instrument adapted and providing for the measurement of a change in concentration of gas or gases produced in a closed vial or vessel, this measurement utilizing infrared energy for said measurement, this instrument including:
   (a) a vial adapted to receive and retain a culture fluid without leakage of fluid;
   (b) a resilient cap means disposed at an upper end of the vial and adapted for penetration by a hollow needle and the like for adding at least one component to the closed vial;
   (c) a core module providing means for passing therethrough of infrared energy from a source to a detector, this core module providing sealing exclusion of the interior of the vial to atmosphere, said core module including:
   (a 1) a plurality of passageway means from the interior of said vial to and through said passageway;
   (a 2) a sized receiving bore formed in said core module and therethrough;
   (a 3) positioning said core module in the vial so as to be positioned in a determined relationship to a bottom portion of the vial;
   (d) a baffle insert mounted in the bore of said core module, said baffle insert in a mounted condition having means for excluding exterior air and the like from entering that bore portion occupied by said baffle insert, said baffle insert including:
   (b 1) a tubular insert having enlarged end portions adapted to fit within said bore of the core module, and with the intermediate portion formed with a reduced tubular portion providing a space between the outer portion of the insert and the bore of the core module;
   (b 2) a plurality of hole-like passageways through the walls of said tubular insert, these passageways adapted to provide flow means for gases from the interior of the vial through the passageways in the core module, thence through the hole-like passageways in the baffle insert into the inner portion of the baffle insert, these hole-like passageways in the reduced tubular portion; and
   (b 3) window means attached to each end of the tubular insert, these windows adapted to pass infrared energy specific to gases produced in the vial;
   (e) a liquid of specific volume and composition, which volume, when placed in the vial, is below the core module when the vial is arrayed for and in use;
   (f) means for adding at least one other material to the liquid in the vial and, with this addition, generating a gas which flows to the exterior of the baffle insert;
   (g) said detector arrayed so as to receive said infrared energy from said source and converting said received energy to electrical signals and sending said electrical signals to
   (h) a means for measuring the magnitude of said electrical signals and interpreting the magnitude of said electrical signals as a concentration of gas as produced within the vial.

2. An instrument for the measurement of concentration as in claim 1 in which the contents of the vial generate gas because of chemical reactions therein.

3. An instrument for the measurement of concentration as in claim 2 in which the contents of the vial are bacterial nutrients to which blood samples are added.

4. An instrument for the measurement of concentration as in claim 2 in which the vial is one of a plurality of like vials and said vials are moved relative to the infrared energy source and detector so that several vials and the gaseous contents of each vial may be evaluated individually, utilizing the levels of gaseous concentration.

5. An instrument for the measurement of concentration as in claim 4 in which a reference measurement of the infrared transmission through a reference vial is provided, and each measurement of the gases in a vial to be tested is compared to said reference measurement produced by the instrument.

6. An instrument for the measurement of concentration as in claim 5 in which the reference measurements are made in an atmosphere external to the vial, which is substantially free of absorption of infrared energy, and including means to maintain the temperature of that atmosphere at a constant value.

7. An instrument for the measurement of concentration as in claim 6 in which the measuring means includes an electronic memory for recording the magnitude of the gas concentration within each vial at the initial test and comparing it with the magnitude at subsequent tests.

8. An instrument for the measurement of concentration as in claim 7 in which the measuring means includes an algorithm for detecting a geometric increase in the concentration of gas within the vial.

9. An instrument for the measurement of concentration as in claim 4 in which the relative movement of the plurality of vials is provided by a carousel means driven by a motor means.

10. An instrument for the measurement of concentration as in claim 9 in which the carousel includes a removable cover for maintaining the surrounding space around a plurality of vials at a determined level of temperature and atmosphere, and the identification of the vials is displayed by means on the carousel apparatus and with the instrument having means to print measurement results on a paper tape and transport said tape to an attendant.

11. An instrument for the measurement of concentration as in claim 2 in which at least one vial includes an identifying bar code.

12. An instrument for the measurement of concentration as in claim 11 in which the location of each vial is identified with a bar code.

13. An instrument for the measurement of concentration as in claim 11 which includes means for reading the bar codes and means for activating a printer when the difference in the magnitude of gas concentration within a vial exceeds a predetermined amount to print out the number of the vial, the number corresponding to its location in the instrument, and the magnitude of gas concentration.

14. An instrument for the measurement of concentration as in claim 2 in which the vial is of plastic and the resilient cap means is formed with screw threads adapted to mate with threads formed in an an extending neck portion of the vial.

15. An instrument for the measurement of concentration as in claim 2 in which the means for measurement of the magnitude of infrared energy utilizes a microprocessor and the magnitude of said measurement is printed on a strip of paper and the like.

16. An instrument for the measurement of concentration as in claim 1 in which the core module within the vial projects through the walls of said vial and is sealed thereto, and the window means secured at each end of the baffle insert is sealed thereto and is substantially transparent to infrared energy and is substantially impermeable to $CO_2$ gas.

17. An instrument for the measurement of concentration as in claim 16 in which the passageway means in the core module are slot-like apertures, and with the hole-like passageways in the baffle insert offset from said slot-like apertures in the core module.

18. An instrument adapted and providing for the measurement of a change in concentration of gas or gases produced in a closed vial or vessel, this measurement utilizing infrared energy for said measurement, this instrument including;
 (a) a vial adapted to receive and retain a culture fluid without leakage of fluid;
 (b) a resilient cap means disposed at the upper end of the vial and adapted for penetration by a hollow needle and the like for adding at least one component to the closed vial;
 (c) a short absorption cell apparatus adapted to be removably mounted at the top and exterior of said vial and providing sealing exclusion of the vial to the atmosphere, this short absorption cell apparatus including:
  (a 1) a substantially rigid retaining ring-like member having a hollow interior;
  (a 2) window means secured to each end of this ring-like member and providing a sealing exclusion thereof, these windows adapted to pass infrared energy specific to the gas or gases produced in said vial;
  (a 3) a unidirectional valve or vent to the atmosphere of those gases entering the short absorption cell;
  (a 4) a hypodermic needle member secured to said ring-like member and adapted to pierce said resilient cap means and to conduct the gas or gases from the interior of the vial to the interior of the ring-like member, and
  (a 5) bracket means to retain the mounted ring-like member of the short absorption cell apparatus in a secured and oriented position on the vial;
 (d) a liquid of specific volume and composition, which volume, when placed in the vial, is below the absorption cell;
 (e) means for adding at least one other material to the liquid in the vial and, with this addition, generating a gas which flows to the interior of the short absorption cell;
 (f) a infrared detector arrayed so as to receive infrared energy passing through said absorption cell from an infrared source, said detector converting said infrared energy to electrical signals and sending said electrical signals to
 (g) a means for measuring the magnitude of said electrical signal and interpreting the magnitude of said received electrical signal as a concentration of gas as produced within the vial.

19. An instrument for a short absorption cell apparatus as in claim 18 in which the bracket means is a metal strap secured to the retaining ring-like member and adapted so as to retain said absorption cell apparatus so that the IR source and IR detector are positioned adjacent the window means secured to the ring-like member.

20. An instrument for a short absorption cell apparatus as in claim 18 in which the ring-like member is a short length of metal tubing to which the window means is IR transparent and is cemented in place to as to be sealed.

21. An instrument for a short absorption cell apparatus as in claim 18 in which the bracket is of bent sheet metal having a spring-like capability adapted to provide a spring retentive force of the absorption cell device when mounted on the vial.

22. An instrument for a short absorption cell apparatus as in claim 21 in which the vial is made substantially rectangular in configuration, with said bracket adapted to provide positioning and orientation when the device is mounted on the vial.

23. An instrument for a short absorption cell apparatus as in claim 22 in which the vial is formed with an extending neck portion which is sufficiently offset to provide means for orienting the absorption cell device when the needle portion thereof is inserted to and through the resilient cap providing closure of the vial.

24. An instrument for a short absorption cell apparatus as in claim 18 in which the needle is positioned in the assembled absorption cell device so that said needle is adapted to puncture and penetrate the resilient cap intermediate the walls of the extending neck portion of said vial.

25. A method for the measurement of a change in concentration of gas or gases produced in a closed vial or vessel, this measurement utilizing infrared energy for said measurement, this method including the steps of:
(a) providing a vial adapted to receive and retain a culture fluid without leakage of fluid;
(b) disposing a resilient cap means at the upper end of the vial, said cap means adapted for the penetration by a hollow needle and the like, enabling the adding of at least one component to the closed vial;
(c) providing means in a core module for the passing therethrough of infrared energy from a source to a detector, and further providing this core module with a sealing exclusion of the interior of the vial to atmosphere, and forming in said core module:
  (a 1) a plurality of passageway means from the interior of said vial to and through said passageways;
  (a 2) a sized receiving bore in said core module and therethrough;
  (a 3) positioning in said core module in the vial so as to be in a determined relationship to a bottom portion of the vial
(d) mounting a baffle insert in the bore of said core module, with said baffle insert in a mounted condition having means for excluding exterior air and the like from entering that bore portion occupied by said baffle insert, and forming said baffle insert with;
  (b 1) a tubular insert having enlarged end portions adapted to fit within said bore of the core module, and with the intermediate portion formed with a reduced tubular portion providing a space between the outer portion of the insert and the bore of the core module;
  (b 2) a plurality of hole-like passageways through the walls of said tubular insert, these passageways adapted to provide flow means for gases from the interior of the vial through the passageways in the core module, thence through the hole-like passageways in the baffle insert into the inner portion of the baffle insert, these hole-like passageways in the reduced tubular portion, and
  (b 3) attaching a window means to each end of the tubular insert, with each window adapted to pass infrared energy specific to gases produced in the vial;
(e) inserting in a said vial a liquid of specific volume and composition, which volume, when placed in the vial, is below the core module when the vial is arrayed for and in use;
(f) adding at least one other material to the liquid in the vial and, with this addition, generating a gas which flows to the interior of the baffle insert;
(g) Providing said source of infrared energy and said detector, and arraying said detector so as to receive said infrared energy passing through a core module and converting said received infrared energy to electrical signals and
(h) measuring the magnitude of said electrical signals and interpreting the magnitude of electrical signals as a concentration of gas produced within the vial.

26. A method for the measurement of the concentration of gases produced in a closed vial as in claim 25 in which the liquid is a bacterial nutrient and includes adding at least one blood sample to said bacterial nutrient.

27. A method for the measurement of the concentration of gases produced in a closed vial as in claim 26 which further includes the step of preparing a plurality of substantially like vials and mounting said vials in a carousel, and moving said carousel and the vials therein relative to the infrared energy source and detector so that several vials and the gaseous contents of each vial may be evaluated individually, utilizing the levels of gaseous concentration.

28. A method for the measurement of the concentration of gases produced in a closed vial as in claim 27 which includes providing the carousel with a retentive cover so that calibrating measurements are made in an atmosphere external to the vial, which is substantially free of absorption of infrared energy, and including means to maintain the temperature of that atmosphere at a constant value.

29. A method for the measurement of the concentration of gases produced in a closed vial as in claim 28 which includes providing in the measuring means an electronic memory for recording the magnitude of the gas concentration within each vial at the initial test and comparing it with the magnitude at subsequent tests.

30. A method for the measurement of the concentration of gases produced in a closed vial as in claim 25 which further includes providing on each vial an identifying bar code.

31. A method for the measurement of the concentration of gases produced in a closed vial as in claim 30 which further includes means for reading the bar codes and means for activating a printer when the difference in the magnitude of gas concentration within a vial exceeds a predetermined amount to print out the number of the vial, the number corresponding to its location in the instrument, and the magnitude of gas concentration.

32. A method for the measurement of a change in the concentration of gas or gases produced in a closed vial or vessel, this measurement utilizing infrared energy for said measurement, this method including the steps of:
(a) providing a vial adapted to receive and retain a culture fluid without leakage of the fluid;
(b) disposing a resilient cap means at the upper end of the vial, said cap means adapted for penetration by a hollow needle and the like, enabling the adding of at least one component to the closed vial;
(c) providing a short absorption cell apparatus in way of infrared energy for the passing through of said infrared energy from a source to a detector, and further providing this short cell with a sealing exclusion of the interior of the vial to atmosphere, the construction and use including the method step of:
  (a 1) arraying a substantially rigid retaining ring-like member having a hollow interior;

(a 2) securing window means to each end of this ring-like member and providing a sealing exclusion thereof, these windows adapted to pass infrared energy specific to the gas or gases produced in said vial;

(a 3) mounting a unidirectional valve or vent to the atmosphere for venting those gases entering the short absorption cell;

(a 4) securing a hypodermic needle member to said ring-like member and adapting said needle so as to pierce said resilient cap means and to conduct the gas or gases from the interior of the vial to the interior of the ring-like member, and (a 5) forming and retaining a bracket means on and to the mounted ring-like member of the short absorption cell apparatus so as to retain said short absorption cell in a desired oriented position on the vial;

(d) inserting into the interior of the vial a liquid of a specific volume and composition, which volume, when placed in a vial, is below the absorption cell;

(e) adding at least one other material to the liquid in the vial and, with this addition, generating a gas which flows to the interior of the short absorption cell;

(f) providing said infrared source and said detector, and arraying said detector so as to receive said infrared energy passing through said absorption cell from said source, said detector converting said infrared energy to electrical signals and;

(g) providing an evaluating means for measuring the magnitude of said electrical signals and interpreting the magnitude of the electrical signals as a concentration of gas produced within the vial.

33. A method for the measurement of the concentration of gases produced in a closed vial as in claim 32 which includes forming the absorption cell with the ring-like member as a short length of metal/or plastic tubing and with the window means as IR transparent, and cementing said window means to the end faces of said ring-like member so as to seal the interior of the absorption cell.

34. A method for the measurement of the concentration of gases produced in a closed vial as in claim 32 which includes forming the vial as a substantially rectangular configuration, and adapting said bracket to provide positioning and orientation when said cell is mounted on the vial.

35. A method for the measurement of the concentration of gases produced in a closed vial as in claim 34 which includes forming the vial with an extending neck portion which is sufficiently offset to provide means for orienting the absorption cell device when the needle portion thereof is inserted to and through the resilient cap providing closure of the vial.

36. An instrument adapted and providing for the measurement of a change in the concentration of gas or gases produced in a closed vial or vessel, this measurement utilizing infrared energy for said measurement, this instrument including:

(a) a vial adapted to receive and retain a culture fluid without leakage of fluid;

(b) a resilient cap means disposed at the upper end of the vial and adapted for penetration by a hollow needle and the like for adding at least one component to the closed vial;

(c) a short absorption cell apparatus adapted to be removably mounted at the top and exterior of said vial and providing sealing exclusion of the vial to atmosphere, this short absorption cell apparatus including:

(a 1) a substantially rigid member having a hollow interior;

(a 2) window means provided by this member and with a sealing exclusion thereof, these window means adapted to pass infrared energy specific to the gas or gases produced in said vial;

(a 3) a unidirectional valve or vent to the atmosphere of those gases entering the short absorption cell;

(a 4) a hypodermic needle member secured to said rigid member and adapted to pierce said resilient cap means and to conduct the gas or gases from the interior of the vial to the interior of the rigid member, and (a 5) means to retain the rigid member of the short absorption cell apparatus in a secured and oriented position on the vial;

(d) a liquid of specific volume and composition, which volume, when placed in the vial, is below the absorption cell;

(e) means for adding at least one other material to the liquid in the vial and, with this addition, generating a gas which flows to the interior of the short absorption cell;

(f) a detector arrayed so as to receive said infrared energy passing through said absorption cell from an infrared source and converting said received energy into electrical signals and (g) a means for measuring the magnitude of said electrical signal and to interpret the magnitude of electrical signal as a concentration of gas as produced within the vial.

37. An instrument for a short absorption cell apparatus as in claim 36 in which the means to retain the rigid member is a metal or plastic strap secured to said rigid member.

38. A method for the measurement of a change in concentration of gas or gases produced in a closed vial or vessel, this measurement utilizing infrared energy for said measurement, this method including the steps of:

(a) providing a vial adapted to receive and retain a culture fluid without leakage of fluid;

(b) disposing a resilient cap means at the upper end of the vial, said cap means adapted for penetration by a hollow needle and the like, enabling the adding of at least one component to the closed vial;

(c) providing a short absorption cell apparatus in way of infrared energy for the passing therethrough of infrared energy from a source to a detector, and further providing this short cell with a sealing exclusion of the interior of the vial to the atmosphere, the construction and use including the method of:

(a 1) arraying a substantially rigid member having a hollow interior;

(a 2) providing window means to this member and with a sealing exclusion thereof, these window means adapted to pass infrared energy specific to the gas or gases produced in said vial;

(a 3) mounting a unidirectional valve or vent to the atmosphere for venting those gases entering the short absorption cell;

(a 4) securing a hypodermic needle member to said member and adapting said needle so as to pierce said resilient cap means and to conduct the gas or gases from the interior of the vial to the interior of the rigid member, and (a 5) forming and retaining a bracket means on the rigid member of the short absorption cell apparatus so as to retain said short absorption cell in desired oriented position on the vial;

(d) inserting into the interior of the vial a liquid of specific volume and composition, which volume, when placed in a vial, is below the absorption cell;

(e) adding at least one material to the liquid in the vial and, with this addition, generating a gas which flows to the interior of the short absorption cell;

(f) providing a source of said infrared energy and a detector, and arraying said detector so as to receive said energy passing through said absorption cell from said source and convert said received infrared energy to electrical signals (g) providing an evaluating means for measuring the magnitude of said electrical signals and interpreting the magnitude of said electrical signals as a concentration of gas as produced within the vial.

* * * * *